US 11,774,390 B2

(12) United States Patent
Burkey et al.

(10) Patent No.: US 11,774,390 B2
(45) Date of Patent: Oct. 3, 2023

(54) SENSOR FOR UNDERGROUND SOIL MEASUREMENT

(71) Applicant: REALMFIVE, Inc., Lincoln, NE (US)

(72) Inventors: Brant Burkey, Denton, NE (US); Dan Pickerill, Milford, NE (US)

(73) Assignee: KLA Corporation, Milpitas, CA (US)

( * ) Notice: Subject to any disclaimer, the term of this patent is extended or adjusted under 35 U.S.C. 154(b) by 0 days.

(21) Appl. No.: 17/373,527

(22) Filed: Jul. 12, 2021

(65) Prior Publication Data

US 2021/0341407 A1    Nov. 4, 2021

Related U.S. Application Data

(63) Continuation-in-part of application No. 16/215,261, filed on Dec. 10, 2018, now Pat. No. 11,231,383.

(60) Provisional application No. 63/050,660, filed on Jul. 10, 2020, provisional application No. 62/596,444, filed on Dec. 8, 2017.

(51) Int. Cl.
| | |
|---|---|
| *G01N 27/22* | (2006.01) |
| *G01D 21/02* | (2006.01) |
| *G01N 33/24* | (2006.01) |
| *H04W 84/18* | (2009.01) |

(52) U.S. Cl.
CPC .......... *G01N 27/223* (2013.01); *G01D 21/02* (2013.01); *G01N 33/246* (2013.01); *G01N 2033/245* (2013.01); *H04W 84/18* (2013.01)

(58) Field of Classification Search
None
See application file for complete search history.

(56) References Cited

U.S. PATENT DOCUMENTS

| | | | |
|---|---|---|---|
| 5,442,293 A * | 8/1995 | Lange | G01N 27/223 324/696 |
| 6,388,453 B1 | 5/2002 | Greer | |
| 8,035,403 B1 | 10/2011 | Campbell et al. | |
| 8,354,852 B1 | 1/2013 | Campbell et al. | |

(Continued)

FOREIGN PATENT DOCUMENTS

| | | |
|---|---|---|
| KR | 20160107977 A | 9/2016 |
| WO | 2017185134 A1 | 11/2017 |

OTHER PUBLICATIONS

International Search Report and Written Opinion dated Apr. 25, 2019 for PCT/US2018/064772.

*Primary Examiner* — Paul M. West
*Assistant Examiner* — Mark A Shabman
(74) *Attorney, Agent, or Firm* — Suiter Swantz pc llo

(57) ABSTRACT

A sensor probe for underground soil measurement is provided. The sensor probe includes one or more first sensor circuits, one or more second sensor circuits, a power supply, and a processor. The processor is configured to control at least one of the one or more first sensor circuits or the one or more second sensor circuits. One or more of the first sensor circuits include an oscillator configured to generate a periodic wave, and a transmitter configured to transmit one or more signals. One or more of the second sensor circuits includes an oscillator configured to generate a periodic wave, and a probe element configured to receive the one or more signals via at least one of the transmitter of the one or more first sensor circuits or a transmitter of one or more additional first sensor circuits of an additional sensor probe.

21 Claims, 11 Drawing Sheets

(56) References Cited

U.S. PATENT DOCUMENTS

| | | |
|---|---|---|
| 8,368,529 B1 | 2/2013 | Campbell et al. |
| 8,374,553 B1 | 2/2013 | Campbell et al. |
| 8,565,927 B1 | 10/2013 | Campbell et al. |
| 8,682,493 B1 | 3/2014 | Campbell et al. |
| 9,532,118 B2 | 12/2016 | Vuran et al. |
| 9,829,869 B2 | 11/2017 | Ersavas et al. |
| 9,872,445 B2 | 1/2018 | Cline et al. |
| 9,949,450 B2 | 4/2018 | Richings et al. |
| 2009/0007706 A1* | 1/2009 | Hitt ............... A01G 25/167 73/866 |
| 2009/0168678 A1 | 7/2009 | Han et al. |
| 2009/0302870 A1 | 12/2009 | Paterson et al. |
| 2011/0035059 A1 | 2/2011 | Ersavas |
| 2013/0207771 A1 | 8/2013 | Ersavas et al. |
| 2015/0366149 A1 | 12/2015 | Canyon et al. |
| 2016/0029568 A1 | 2/2016 | Anjum |
| 2016/0183484 A1* | 6/2016 | Richings, Sr. ....... A01G 25/167 239/11 |
| 2016/0255763 A1* | 9/2016 | Canyon ............... A01B 79/005 |
| 2019/0187086 A1 | 6/2019 | Burkey et al. |

\* cited by examiner

SENSOR FOR UNDERGROUND SOIL MEASUREMENT

CROSS-REFERENCE TO RELATED APPLICATION

The present application claims the benefit under 35 U.S.C. § 119(e) of U.S. Provisional Application Ser. No. 63/050,660, filed Jul. 10, 2020, and also constitutes a continuation-in-part (CIP) of U.S. Non-Provisional patent application Ser. No. 16/215,261, filed Dec. 10, 2018, which is a non-provisional application of U.S. Provisional Application Ser. No. 62/596,444, filed Dec. 8, 2017, whereby each of the above-listed patent applications is incorporated herein by reference in the entirety.

TECHNICAL FIELD

The present disclosure relates generally to material sensors, and, more particularly, to a system and method of sub-surface material sensors.

BACKGROUND

In a wide range of industries, from agricultural industries, turf care industries, to construction and commodity storing industries, it may be desirable to determine characteristics of a material not only on the surface of the material, but below the surface as well. Accordingly, buried and/or sub-surface sensors are sometimes used to obtain one or more measurements regarding sub-surface characteristics and conditions. These sub-surface sensors may be desirable when obtaining measurements of sub-surface characteristics is not otherwise feasible and/or easily conducted. However, previous sub-surface sensor systems have faced a number of limitations and drawbacks.

Buried and/or submerged sensors are sometimes used to obtain one or more measurements regarding sub-surface material characteristics, such as sub-surface moisture levels and sub-surface material type (e.g., soil type). However, previous sub-surface sensor systems have suffered from a number of limitations. Previous sub-surface sensor systems are generally unable to determine a sub-surface material type without additional steps and/or equipment.

Another limitation of previous sub-surface sensor systems is their inability to use a varied frequency in measuring sub-surface material characteristics. For example, previous sub-surface sensor systems utilize a fixed frequency capacitance method to measure sub-surface material characteristics. In this regard, the measurements may be influenced by one or more characteristics of a sub-surface material, and may result in an adverse effect on measurement output.

One variation of existing soil moisture sensors often utilizes an oscillator comprising a fixed inductor wired in parallel with a probe capacitor. The probe capacitor may be configured to change capacitance based on the amount of moisture in the soil surrounding the probe capacitor. This inductor and capacitor circuit may be referred to as an "LC circuit." Furthermore, the LC circuit may set the frequency of the oscillator, this frequency having a fixed range. As the moisture level in the soil surrounding the probe capacitor changes, the capacitance of the probe capacitor may change, thereby changing the frequency of the oscillator. The frequency of the oscillator may subsequently be divided down digitally to a measurable frequency, which may then be converted to a moisture content level using a calibrated capacitance/moisture level formula.

Another variation of existing soil moisture sensors often utilizes an oscillator comprising a fixed resistor wired in series with a capacitor connected to ground (i.e., an RC circuit). The RC circuit functions as a filter, blocking certain frequencies. Thus, this previous variation functions by the oscillator sending a fixed frequency through a filter and measuring the attenuation after the frequency has passed through the filter. The frequency of the oscillator must be fixed in order to get accurate soil moisture measurements.

Both of these previous variations require calibration, due to the influence that soil type has on the frequency measurements. Also, both existing variations require that the frequency be fixed, meaning the frequency cannot be swept over a range. Further, neither of these existing variations are able to determine and account for different soil types which is necessary for understanding how much moisture is available to be utilized by plants, crops, and the like.

Therefore, it would be desirable to provide a system and method which cure one or more of the shortfalls of the previous approaches identified above.

SUMMARY

A sensor probe is disclosed, in accordance with one or more embodiments of the present disclosure. In one illustrative embodiment, the probe includes one or more first sensor circuits. In another illustrative embodiment, the probe includes one or more second sensor circuits. In another illustrative embodiments, the probe includes a power supply. In another illustrative embodiment, the probe includes a processor configured to control at least one of the one or more first sensor circuits or the one or more second sensor circuits. In one illustrative embodiment, the one or more first sensor circuits include one or more oscillators configured to generate a periodic wave. In another illustrative embodiment, the one or more first sensor circuits include a transmitter configured to transmit one or more signals. In one illustrative embodiment, the one or more second sensor circuits include one or more oscillators configured to generate a periodic wave. In another illustrative embodiment, the one or more second sensor circuits include a probe element configured to receive the one or more signals via the transmitter of the one or more first sensor circuits.

A system is disclosed, in accordance with one or more embodiments of the present disclosure. In one illustrative embodiment, the system may include a data gateway. In another illustrative embodiment, the system may include a plurality of probes communicatively coupled to the data gateway. In one illustrative embodiment, at least one probe of the plurality of probes may include one or more sensor circuits, where the one or more sensor circuits may include at least one of an oscillator, a transmitter, a probe element, or a radio frequency detector. In another illustrative embodiment, at least one probe of the plurality of probes may include a power supply. In another illustrative embodiment, at least one probe of the plurality of probes may include a processor communicatively coupled to the one or more sensor circuits. In one illustrative embodiment, the processor is configured to receive data collected by the one or more sensor circuits. In another illustrative embodiment, the processor is configured to store data received by the one or more sensor circuits. In another illustrative embodiment, the processor is configured to generate one or more signals to adjust one or more characteristics of the one or more sensor circuits in response to the data received.

A method is disclosed, in accordance with one or more embodiments of the present disclosure. In one illustrative embodiment, the method may include, but is not limited to, generating a lookup table based on a plurality of known soil type values. In another illustrative embodiment, the method may include, but is not limited to, transmitting one or more signals through a volume of soil. In another illustrative embodiment, the method may include, but is not limited to, measuring the one or more signals through the volume of soil. In another illustrative embodiment, the method may include, but is not limited to, determining one or more soil types by comparing the one or more measured signals to the plurality of known soil type values in the lookup table.

It is to be understood that both the foregoing general description and the following detailed description are exemplary and explanatory only and are not necessarily restrictive of the invention as claimed. The accompanying drawings, which are incorporated in and constitute a part of the specification, illustrative embodiments of the invention and together with the general description, serve to explain the principles of the invention.

BRIEF DESCRIPTION OF DRAWINGS

The numerous advantages of the disclosure may be better understood by those skilled in the art by reference to the accompanying figures in which.

DETAILED DESCRIPTION

Figure 1:
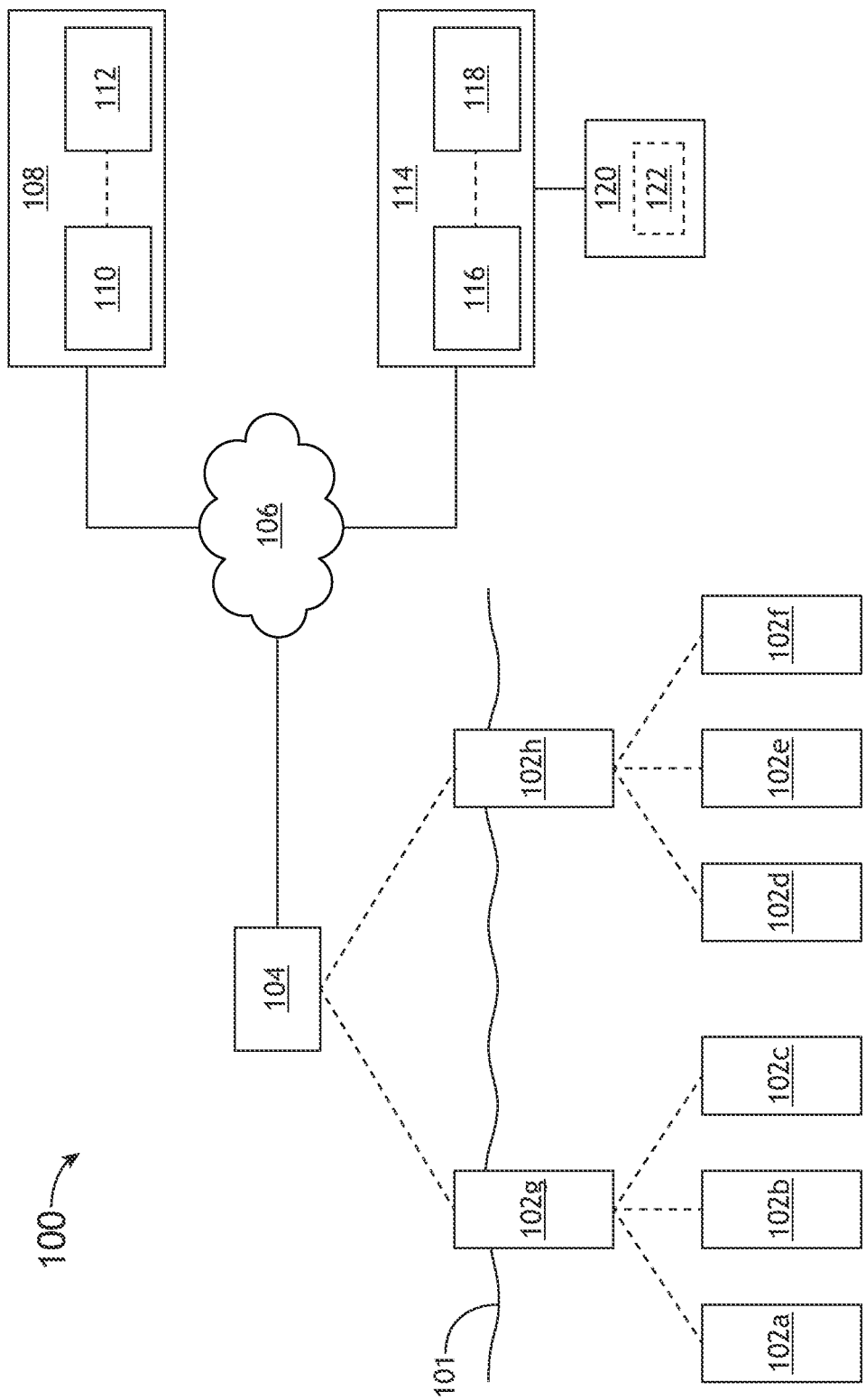
FIG. 1 illustrates a simplified block diagram of an underground soil measurement system, in accordance with one or more embodiments of the present disclosure.

Reference will now be made in detail to the subject matter disclosed, which is illustrated in the accompanying drawings. The present disclosure has been particularly shown and described with respect to certain embodiments and specific features thereof. The embodiments set forth herein are taken to be illustrative rather than limiting. It should be readily apparent to those of ordinary skill in the art that various changes and modifications in form and detail may be made without departing from the spirit and scope of the disclosure.

Buried and/or submerged sensors are sometimes used to obtain one or more measurements regarding sub-surface material characteristics, such as sub-surface moisture levels and sub-surface material type (e.g., soil type). However, previous sub-surface sensor systems have suffered from a number of limitations. Previous sub-surface sensor systems are generally unable to determine a sub-surface material type without additional steps and/or equipment.

One variation of existing soil moisture sensors often utilizes an oscillator comprising a fixed inductor wired in parallel with a probe capacitor. The probe capacitor may be configured to change capacitance based on the amount of moisture in the soil surrounding the probe capacitor. This inductor and capacitor circuit may be referred to as an "LC circuit." Furthermore, the LC circuit may set the frequency of the oscillator, this frequency having a fixed range. As the moisture level in the soil surrounding the probe capacitor changes, the capacitance of the probe capacitor may change, thereby changing the frequency of the oscillator. The frequency of the oscillator may subsequently be divided down digitally to a measurable frequency, which may then be converted to a moisture content level using a calibrated capacitance/moisture level formula.

Another variation of existing soil moisture sensors often utilizes an oscillator comprising a fixed resistor wired in series with a capacitor connected to ground (i.e., an RC circuit). The RC circuit functions as a filter, blocking certain frequencies. Thus, this previous variation functions by the oscillator sending a fixed frequency through a filter and measuring the attenuation after the frequency has passed through the filter. The frequency of the oscillator must be fixed in order to get accurate soil moisture measurements.

Both of these previous variations require calibration, due to the influence that soil type has on the frequency measurements. Also, both existing variations require that the frequency be fixed, meaning the frequency cannot be swept over a range. Further, neither of these existing variations are able to determine and account for different soil types which is necessary for understanding how much moisture is available to be utilized by plants, crops, and the like.

Another limitation of previous sub-surface sensor systems is their inability to use a varied frequency in measuring sub-surface material characteristics. For example, previous sub-surface sensor systems utilize a fixed frequency capacitance method to measure sub-surface material characteristics. In this regard, the measurements may be influenced by one or more characteristics of a sub-surface material, and may result in an adverse effect on measurement output.

Accordingly, embodiments of the present disclosure are directed to at least one sub-surface sensor probe which utilizes one or more sensor circuits to communicatively couple the sub-surface sensor probe to an above-ground data gateway. Additional embodiments of the present disclosure are directed to a system which utilizes wireless data transmission to transmit data below ground between sub-surface sensor probes. Additional embodiments of the present disclosure are directed to the use of a data gateway configured to communicatively couple to one or more sub-surface sensor circuits of the sub-surface sensor probe in order to reduce recurring data transmission costs. Further embodiments of the present disclosure are directed to at least one sensor probe which can more efficiently and effectively measure sub-surface moisture levels in a sub-surface sensor circuit system.

Reference will now be made in detail to the subject matter disclosed, which is illustrated in the accompanying drawings.

Referring generally to FIGS. 1-7, a system and method for underground soil measurement are disclosed, in accordance with one or more embodiments of the present disclosure.

FIG. 1 illustrates a simplified block diagram of a sub-surface sensor system 100, in accordance with one or more embodiments of the present disclosure. System 100 may include, but is not limited to, one or more sensor probes 102, a data gateway 104, a network 106, a server 108, a controller 114, and a user interface 120.

In one embodiment, the one or more sensor probes 102 may be positioned below the surface 101 of a material and configured to measure and/or collect data regarding one or more sub-surface material characteristics. For example, as shown in FIG. 1, sensor probes 102a, 102b, 102c, 102d, 102e, and 102f may be positioned under the surface 101 of the ground (e.g., buried within the soil). The one or more sub-surface material characteristics may include, but are not limited to, moisture levels, electroconductivity levels, temperatures, chemical compositions, pressures, nutrient levels, and the like. For example, system 100 may be implemented in an agricultural setting, in which the one or more sub-surface probes 102 are buried within agricultural fields and configured to measure sub-surface soil characteristics, including soil moisture levels, soil electroconductivity levels, soil temperatures, nutrient levels, gases, particulate constituents, biological pathogens, pH, and the like.

As will be described in further detail herein, it is contemplated herein that the sensor probes 102 of the present disclosure may be implemented in a wide variety of contexts, and may be used to measure sub-surface characteristics of any material. For example, sensor probes 102 may be configured to measure sub-surface material characteristics of soil, liquids (e.g., water, oil, liquid fertilizer), volumes of commodities (e.g., potatoes, corn, grain, wheat, and the like), biomass, landfill material, concrete, bulk storage materials (e.g., dry fertilizer, salt, sand, gravel, and the like) and the like. In this regard, although system 100 may be described as being implemented in an agricultural context, this is solely for illustrative purposes, and is not to be regarded as a limitation of the present disclosure, unless noted otherwise herein.

The sub-surface sensor probes (e.g., sensor probes 102a, 102b, 102c, 102d, 102e, and 102f) may be positioned below the surface 101 a sufficient depth in order to avoid being damaged by equipment or operations, such as tilling equipment, planting equipment, harvesting equipment, and the like. In this regard, sensor probes 102 may be installed below relevant operating depths of equipment which may be operating within the same area as system 100. It is further contemplated herein that the sub-surface sensor probes 102a-102f may be positioned below the surface 101 at a depth which allows for reliable data transmission to components above the surface 101 of the material (e.g., sensor probes 102g, 102h, data gateway 104, and the like).

For the purposes of the present disclosure, sensor probes 102 which are positioned completely below the surface 101 of a material (e.g., sensor probes 102a-102f) may be referred to as "sub-surface sensor probes 102." Conversely, sensor probes 102 which are positioned partially or completely above the surface 101 of a material (e.g., sensor probes 102g, 102h) may be referred to as "surface sensor probes 102."

In another embodiment, the one or more sub-surface sensor probes 102a-102f may be configured to store collected data in memory. In another embodiment, the one or more sub-surface sensor probes 102a-102f may be configured to transmit collected and stored data to an additional sensor probe 102. For example, as shown in FIG. 1, sub-surface sensor probes 102a, 102b, 102c and sub-surface sensor probes 102d, 102e, 102f may be configured to transmit collected and stored data to sensor probe 102g and sensor probe 102h, respectively. The sub-surface sensor probes 102a-102f may be configured to transmit data to surface sensor probes 102g, 102h using any type of wireless communication technique known in the art including, but not limited to, radio frequency (RF) protocols, Bluetooth protocols, GSM, GPRS, DCMA, EV-DO, EDGE, WiMAX, 4G, 4G LTE, 5G, 6G, WiFi protocols, RF, LoRa, and the like. By way of another example, sub-surface sensor probes 102a-102f may be configured to transmit data to surface sensor probes 102g, 102h using ZigBee, SigFox, NB-IOT, and the like.

For example, sub-surface sensor probes 102a-102f may be configured to transmit data to surface sensor probes 102g, 102h using LoRa. LoRa wireless radio technology is often used to transmit small amounts of data over longer distances. It is noted herein that LoRa radio technology has been found to provide reliable long-distance data transmission even in conditions which would ordinarily pose issues using other data transmission techniques. For instance, agricultural crop canopies, such as corn, may strongly absorb radio waves, leading to poor RF transmission in such conditions. On the other hand, LoRa has been found to provide reliable long-distance transmissions in such conditions. These characteristics of LoRa may make LoRa a good candidate for data transmission in sub-surface environments, such as system 100. However, it is noted herein that LoRa wireless radio technology is often used to transmit small amounts of data over longer distances, but may be inappropriate to wirelessly transmit large amounts of data. As such, alternative wireless data transmission techniques may be required in systems which require large amounts of data transmission.

In another embodiment, surface sensor probe 102g and surface sensor probe 102h may be configured to store data received by sub-surface sensor probes 102a, 102b, 102c, and sub-surface sensor probes 102d, 102e, and 102f, respectively. Furthermore, surface sensor probes 102g, 102h may be configured to measure and/or collect data regarding one or more sub-surface material characteristics.

As noted previously herein, the wireless data transmission below ground may be limited by technical and environmental factors. The efficiency and range of wireless data transmission may be significantly decreased when transmitting data below the surface of a material. Particularly, it is noted herein that radio and other waves may be absorbed by biomass, such as soil, crops, foliage, and the like. Furthermore, sub-surface material may obstruct the efficient transmission of data. In this regard, in another embodiment, surface sensor probes 102g, 102h may be positioned such that at least a portion of the surface sensor probes 102g, 102h are positioned above the surface 101 of the material. By positioning at least a portion of surface sensor probes 102g, 102h above the surface 101 of the material, the effective data transmission range of sensor probes 102g, 102h may be significantly improved. It is further noted herein that the ability of surface sensor probes 102g, 102h to receive, store, and transmit data collected by the sub-surface sensor probes 102a-102f (e.g., "store-and-forward") may allow the surface sensor probes 102g, 102h to effectively increase the data transmission range of the sub-surface sensor probes 102a-102f. For the purposes of the present disclosure, the sensor probes 102g, 102h may be said to function as "repeaters" and/or "store-and-forward sensor probes" in that they are configured to receive data from other sensor probes 102, store the received data, and transmit the stored data to other components in system 100.

In one embodiment, sensor probes 102g, 102h are configured to transmit stored data to data gateway 104. The sensor probes 102g, 102h may be communicatively coupled to the data gateway 104 using any wired or wireless communication technique known in the art including, but not limited to, ZigBee, SigFox, NB-IOT, radio frequency (RF) protocols, Bluetooth protocols, GSM, GPRS, DCMA, EV-DO, EDGE, WiMAX, 4G, 4G LTE, 5G, 6G, WiFi protocols, RF, LoRa, and the like.

It is noted herein that the configuration of system 100 with one or more sub-surface sensor probes 102 (e.g., sensor probes 102a-102f) transmitting collected and stored data to one or more surface sensor probes 102 (e.g., sensor probes 102g, 102h) may provide a number of advantages over prior approaches. First, transmitting data from sub-surface sensor probes 102a-102f to surface sensor probes 102g, 102h may effectively increase the data transmission range of the sub-surface sensor probes 102a-102f. Secondly, embodiments which utilize multiple sub-surface sensor probes 102 for each surface sensor probe 102g, 102h may minimize the amount of equipment and components which may be susceptible to damage by above-ground operations. For example, by minimizing the number of surface sensor probes 102g, 102h, system 100 may effectively minimize the number of surface sensor probes 102g, 102h which may be damaged by planting equipment, tilling equipment, irrigation equipment, spraying equipment, harvesting equipment, and the like. By burying sub-surface sensor probe 102a-102f below the surface 101 a sufficient depth, system 100 may effectively reduce the amount of equipment which is susceptible to damage through ordinary operations.

An additional advantage associated with system 100 is the reduction in the amount of above-ground equipment, and therefore the reduction of annual labor costs. As noted previously herein, above-ground components may have to be removed before various operations can take place. For example, above-ground sensors may have to be removed prior to tilling, planting, and harvesting operations. However, utilizing system 100, the number of components (e.g., surface sensor probes 102g, 102h) which are positioned above the surface 101 may be minimized, thereby minimizing the number of components which must be removed prior to operations on a regular or semi-regular basis. This reduction may be translated into fewer man hours required to remove equipment prior to operations, lower installation and removal costs, and thus lower annual labor costs. This effectively reduces the annual operating cost of each individual sensor probe 102.

Another advantage provided by the configuration of system 100 is the reduction of recurring data transmission costs. As noted previously herein, previous systems communicatively couple each sub-surface sensor directly to a data processing or communications module. This repetitive data transmission results in recurring and repetitive data transmission costs. By communicatively coupling a subset of sensor probes 102 of system 100 to the data gateway 104 (e.g., sensor probes 102g, 102h), wherein the subset of sensor probes 102 are communicatively coupled to additional sensor probes 102 (e.g., sub-surface sensor probes 102a-102f), system 100 may effectively reduce recurring data transmission costs associated with transmitting data to the data gateway 104 and network 106.

The ability of surface sensor probes 102g, 102h to receive and store data from sub-surface sensor probes 102a-102f may also improve overall data transmission efficiency. For example, obstructions or environmental conditions, such as rain, snow, construction equipment, farming equipment, and the like, may impair the data transmission efficiency between the surface sensor probes 102g, 102h and the data gateway 104. In this regard, when the surface sensor probes 102g, 102h are out of range from the data gateway 104 or otherwise unable to transmit data to the data gateway 104, the surface sensor probes 102g, 102h may be configured to store in memory data collected by the surface sensor probes 102g, 102h and data received from the sub-surface sensor probes 102a-102f. When the data gateway 104 is in range or the surface sensor probes 102g, 102h are otherwise able to transmit data efficiently, the surface sensor probes 102g, 102h may be configured to transmit the data stored in memory.

In an additional and/or alternative embodiment, sensor probes 102g, 102h may comprise only store-and-forward components. For example, sensor probes 102g, 102h may be configured to receive data collected by sensor probes 102a-102f, store received data, and forward stored data to the data gateway 104. In this example, sensor probes 102g, 102h may not include any sensors which are configured to cause sensor probes 120g, 102h to collect data on their own.

In another embodiment, the data gateway 104 of system 100 is configured to receive data from one or more sensor probes 102 (e.g., sensor probes 102g, 102h) and store the data in memory. In another embodiment, the data gateway 104 may be configured to transmit received and stored data to a network 106. As noted previously, the data gateway 104 may be configured to store data in memory when the data gateway 104 is unable to transmit data, and subsequently transmit the stored data when the data gateway 104 becomes communicatively coupled to network 106. The data gateway 104 may be configured to transmit data to network 106 using any type of wireless communication technique known in the art including, but not limited to, radio frequency (RF) protocols, Bluetooth protocols, GSM, GPRS, DCMA, EV-DO, EDGE, WiMAX, 4G, 4G LTE, 5G, 6G, WiFi protocols, RF, LoRa, and the like. In this regard, data gateway 104 may include any network interface known in the art configured to communicatively couple the data gateway 104 to the network 106. In one embodiment, network 106 may comprise a cloud-based network configuration.

In another embodiment, the network 106 is configured to transmit data received from the sensor probes 102 to a server 108. The server 108 may include one or more processors 110 and a memory 112. It is contemplated herein that the server 108 may comprise a remote server configured to carry out one or more of the steps of the present disclosure. In one embodiment, server 108 may include a cloud-based computing platform including, but not limited to, Amazon Web Services (AWS). In one embodiment, one or more processors 110 of server 108 may be configured to store the received data in memory 112. The one or more processors 110 may be further configured to execute a set of program instructions stored in memory 112, the program instructions configured to cause the one or more processors 110 to carry out one or more steps of the present disclosure.

For example, the data collected by the sensor probes 102 may be transmitted to server 108 via network 106. The one or more processors 110 may be configured to time-stamp and store received data in memory 112. The one or more processors 110 may be further configured to filter and sort stored data. The one or more processors 110 may be further configured to perform one or more operations on received and stored data. For example, as will be discussed in greater detail herein, the sensor probes 102 may include capacitive moisture sensors which measure material moisture levels based on calculated capacitance levels. In this regard, the one or more processors 110 may be configured to receive capacitance level readings from the sensor probes 102 and calculate material moisture levels based on the received capacitance level readings. The one or more processors 110 may then be further configured to store calculated moisture levels in memory 112.

In another embodiment, system 100 includes a controller 114 communicatively coupled to the server 108 via network 106. The controller 114 may be configured to receive data collected by the sensor probes 102 via the network 106. The controller 114 may be further configured to receive data generated and/or stored by the server 108 via network 106. In this regard, the controller 114 may include a network interface configured to communicatively couple the controller 114 to the network 106. In one embodiment, the controller 114 includes one or more processors 116 and a memory 118. In another embodiment, the one or more processors 116 may be configured to execute a set of program instructions stored in memory 118, wherein the set of program instructions are configured to cause the one or more processors 116 to carry out the steps of the present disclosure.

For example, the data collected by the sensor probes 102 may be transmitted to controller 114 via network 106. The one or more processors 116 may be configured to time-stamp and store received data in memory 118. The one or more processors 116 may be further configured to filter and sort stored data. The one or more processors 116 may be further configured to perform one or more operations on received and stored data. It is noted herein that the discussion herein regarding server 108, one or more processors 110, and memory 112 may also be regarded as applying to controller 114, one or more processors 116, and memory 118, unless noted otherwise herein. In this regard, any steps of functions carried out by the server 108 may additionally and/or alternatively be carried out by the controller 114, unless noted otherwise herein.

It is further noted herein that the one or more components of system 100 may be communicatively coupled to the various other components of system 100 in any manner known in the art. For example, the server 108, controller 114, one or more processors 110, 116, and memory 112, 118 may be communicatively coupled to each other and other components via a wireline (e.g., copper wire, fiber optic cable, and the like) or wireless connection (e.g., RF coupling, IR coupling, data network communication (e.g., WiFi, WiMax, Bluetooth, 3G, 4G, 4G LTE, 5G, 6G, and the like).

In one embodiment, system 100 may include a user interface 120 communicatively coupled to the controller 114. In one embodiment, the user interface 120 includes a display 122 used to display data of the system 100 to a user. The display 122 of the user interface 120 may include any display known in the art. For example, the display may include, but is not limited to, a liquid crystal display (LCD), an organic light-emitting diode (OLED) based display, or a CRT display. Those skilled in the art should recognize that any display 122 device capable of integration with a user interface 120 is suitable for implementation in the present disclosure. In another embodiment, a user may input selections and/or instructions responsive to data displayed to the user via the user interface 120.

In another embodiment, the user interface 120 may include, but is not limited to, one or more desktops, laptops, tablets, smartphones, smart watches, or the like. In one embodiment, a user may use the user interface 120 in order to view data collected by the sensor probes 102, generated by the one or more processors 110, 116, or stored in memory 112, 118. In another embodiment, the user interface 120 may be configured one or more input commands from a user, wherein the one or more input commands are configured to cause one or more processors to adjust one or more characteristics of system 100.

For example, one or more processors 110, 116 may be configured to transmit one or more alerts to a user, wherein the user interface 120 is configured to display the one or more alerts to the user via the display 122. For example, the one or more processors 110, 116 may be configured to transmit one or more alerts to a user indicating a low moisture level in a section of a field. The one or more alerts generated by system 100 and displayed via display 122 may include any alert known in the art including, but not limited to, automated phone calls, text messages, emails, application notifications, banners, push notifications, and the like.

By way of another example, a farm owner may desire to view temperatures and moisture levels of the soil at various points throughout the farm. It is noted herein that the ability to view soil characteristics (e.g., temperature, moisture levels, electroconductivity levels, and the like) at various points throughout a farm may allow a farm owner or operator to adjust one or more farm characteristics or farming operating parameters in order to more effectively and efficiently operate the farm. For instance, based on moisture levels collected, stored, and displayed to a farm owner via display 122, a farm owner may be able to modify irrigation times, irrigation volumes, fertilizer types, and the like in order to optimize crop growth.

It is noted that additional or alternative embodiments of sub-surface sensor system 100 are described in detail in U.S. patent application Ser. No. 16/215,261, published on Dec. 10, 2018, which is incorporated herein in the entirety.

Figure 2A:
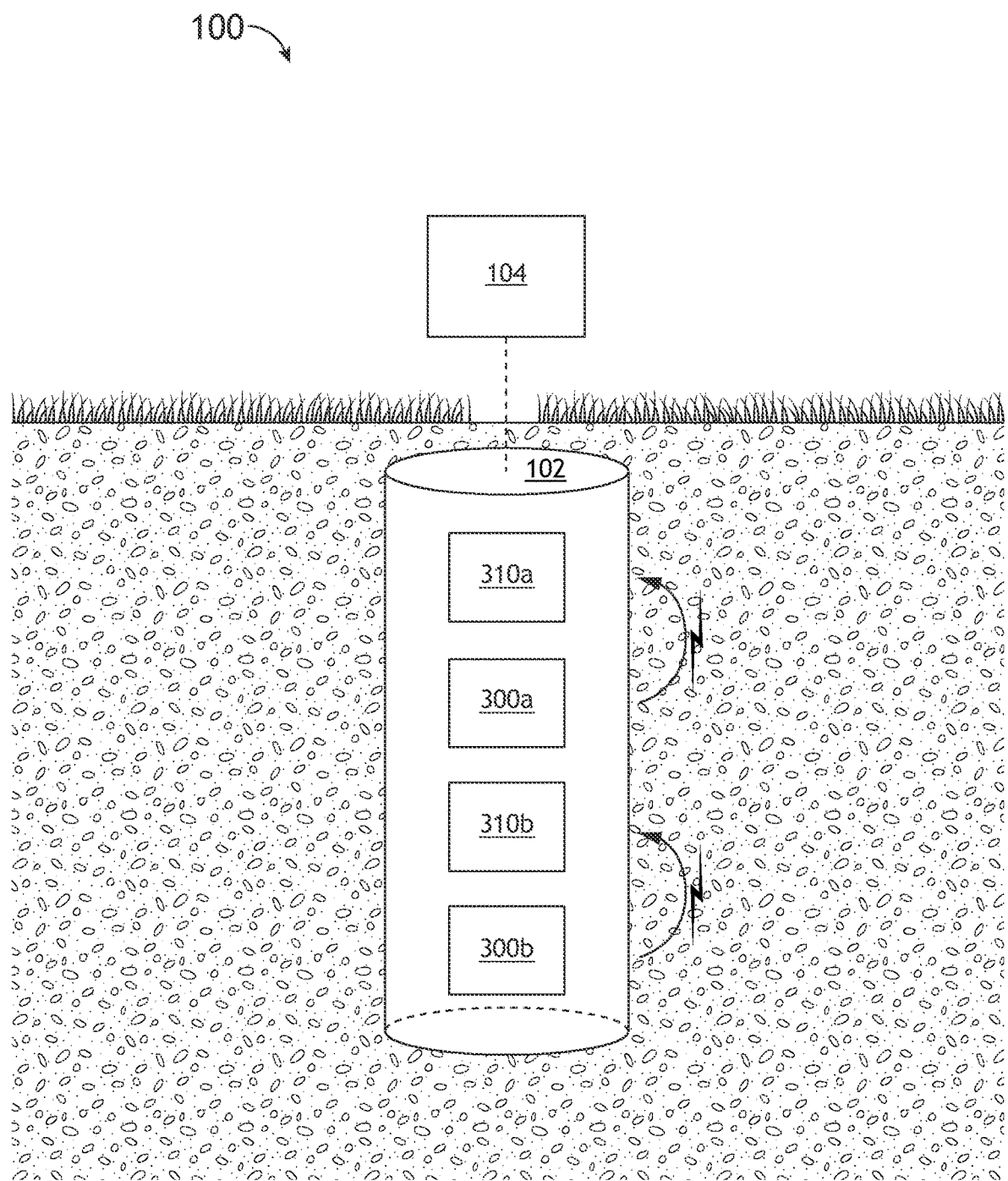
FIG. 2A illustrates a simplified block diagram of an underground soil measurement system, in accordance with one or more embodiments of the present disclosure.
Figure 2B:
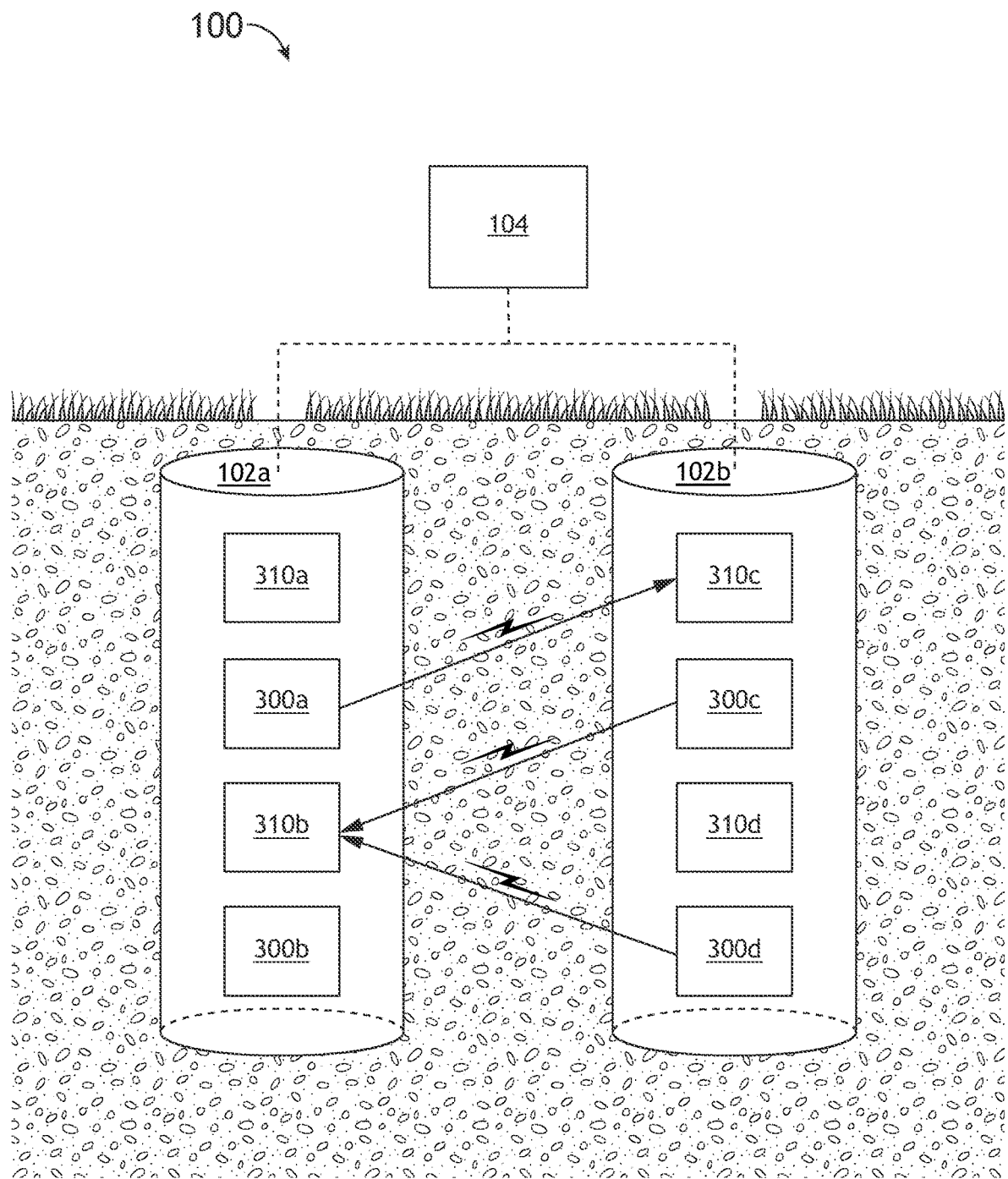
FIG. 2B illustrates a simplified block diagram of an underground soil measurement system, in accordance with one or more embodiments of the present disclosure.

FIGS. 2A and 2B illustrate simplified block diagrams of an underground soil measurement system 100, in accordance with one or more embodiments of the present disclosure. Underground soil measurement systems comprise one or more sensor probes 102, one or more moisture sensors 300 and 310, and one or more data gateways 104.

As illustrated by FIG. 2A, Sensor probes 102 may be communicatively coupled to one or more data gateways 104. One or more moisture sensors 300 may be communicatively coupled to one or more moisture sensors 310 within the same sensor probe. For example, moisture sensor 300$a$ may transmit to moisture sensor 310$a$ and moisture sensor 310$b$ may receive from moisture sensor 300$b$.

Further, one or more moisture sensors 300 may be communicatively coupled to one or more moisture sensors 310 within a different sensor probe 102. For example, as illustrated in FIG. 2B, moisture sensor 300$a$ in sensor probe 102$a$ may transmit to moisture sensor 310$c$ in sensor probe 102$b$. Moisture sensor 300$c$ in sensor probe 102$b$ may transmit to moisture sensor 310$b$ in sensor probe 102$a$. Moisture sensor 310$b$ in sensor probe 102$a$ may also receive from moisture sensor 300$d$ in sensor probe 102$b$.

Figure 2C:
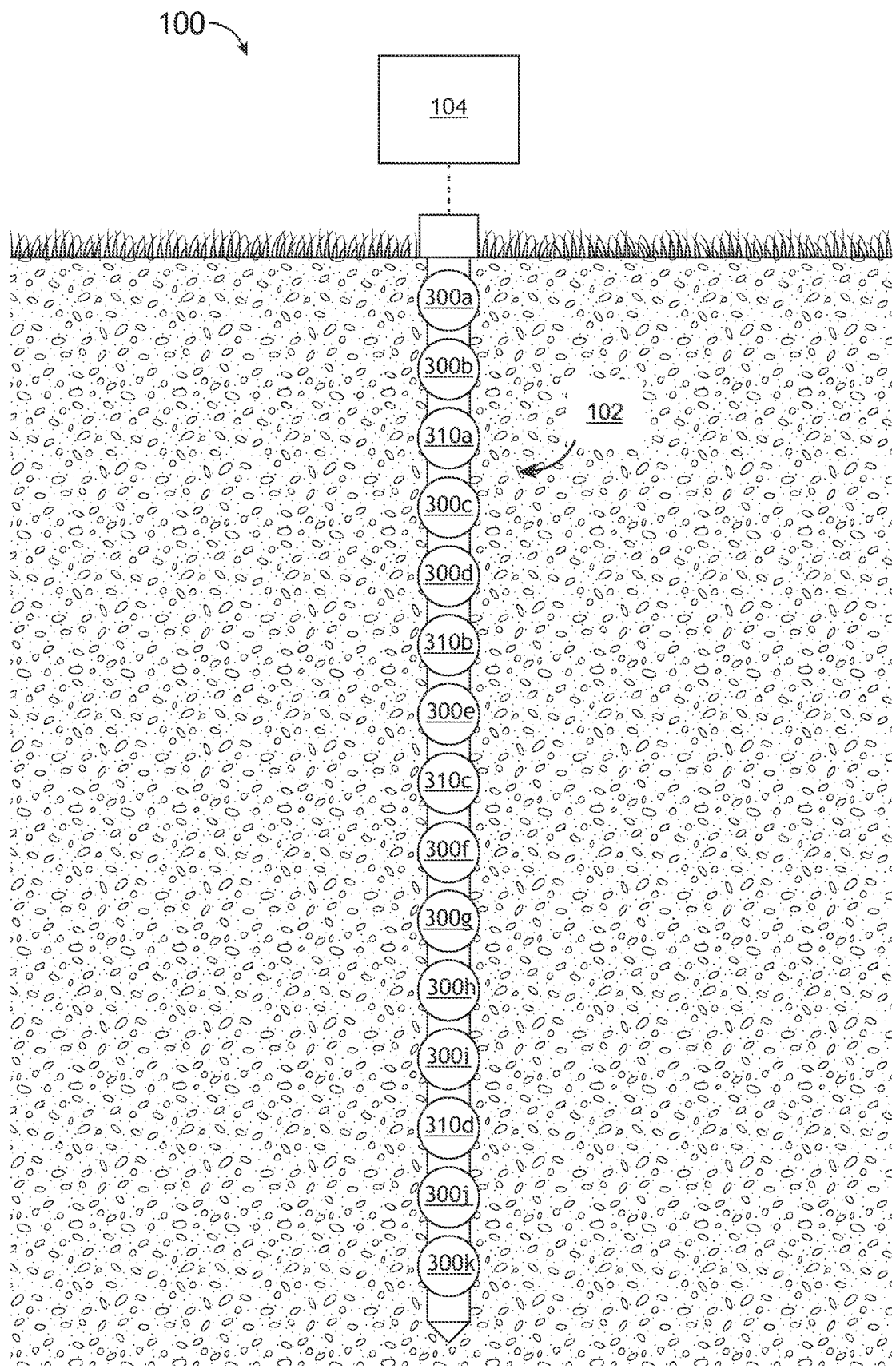
FIG. 2C illustrates a schematic view of an underground soil measurement system, in accordance with one or more embodiments of the present disclosure.

FIG. 2C illustrates a schematic view of an underground soil measurement system 100, in accordance with one or more embodiments of the present disclosure. An underground soil measurement system may comprise one or more sensor probes 102, one or more moisture sensors 310 and 300, and one or more data gateways 104. A sensor probe 102 may contain any combination of moisture sensors 300 and 310. For example, as illustrated by FIG. 2C, moisture sensor probe 102 contains moisture sensors 300*a*, 300*b*, 310*a*, 300*c*, 300*d*, 310*b*, 300*e*, 310*c*, 300*f*, 300*g*, 300*h*, 300*i*, 310*d*, 300*j*, and 300*k*.

Figure 2D:
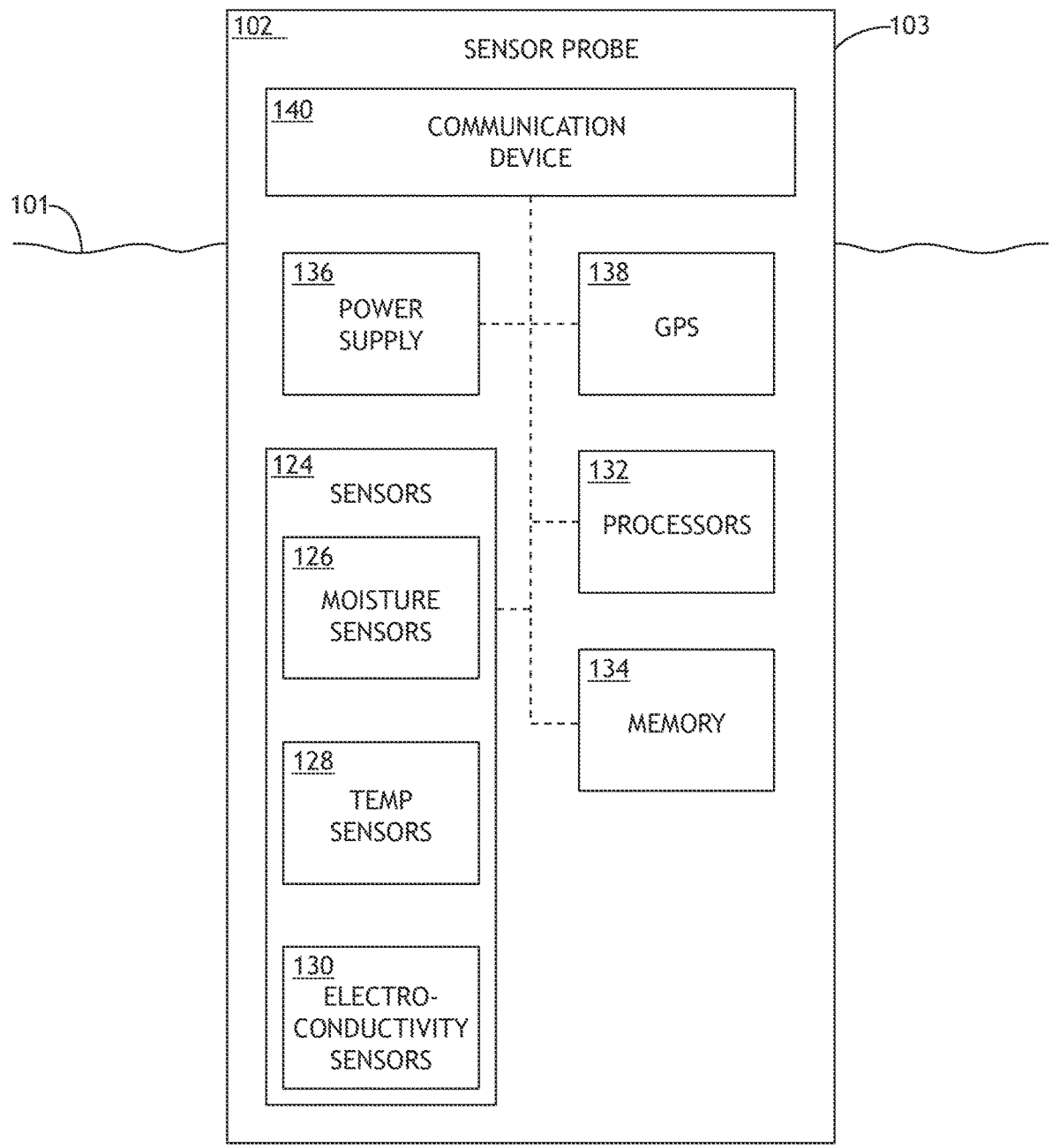
FIG. 2D illustrates a simplified block diagram of a sensor probe, in accordance with one or more embodiments of the present disclosure.

FIG. 2D illustrates a simplified block diagram of a sensor probe 102, in accordance with one or more embodiments of the present disclosure. In embodiments, sensor probe 102 may include, but is not limited to, one or more sensors 124, one or more processors 132, memory 134, a power supply 136, a GPS device 138, and a communication device 140.

It is noted herein that the sensor probes 102, as depicted in FIG. 2D, may be regarded as applying to a sub-surface sensor probes 102 (e.g., sensor probes 102*a*-102*f* in FIG. 1) and/or a surface sensor probes 102 (e.g., sensor probe 102*g*, 102*h* in FIG. 1). For example, as illustrated in FIG. 1, the sensor probe 102 may comprise a surface sensor probe 102*g* in which at least a portion of the sensor probe 102*g* is positioned above the surface 101 of a material. However, this is shown purely for illustration, and is not to be regarded as a limitation of the present disclosure.

In one embodiment, as shown in FIG. 2D, all the components of the sensor probe 102 may be contained within a single sensor probe 102 housing 103. In one embodiment, the one or more sensors 124 of sensor probe 102 include, but are not limited to, one or more moisture sensors 126, one or more temperature sensors 128, and one or more electroconductivity sensors 130. It is contemplated herein that the one or more sensors 124 may include additional and/or alternative sensors including, but not limited to, chemical composition sensors, pressure sensors, nutrient level sensors, pH, constituents, pest sensors, and the like. As noted previously herein, the one or more sensors 124 are configured to collect data regarding one or more sub-surface material characteristics. For example, in embodiments where sensor probes 102 are positioned within the soil of an agricultural or turf setting, the one or more moisture sensors 126 may be configured to collect data regarding moisture levels of the soil, the one or more temperature sensors 128 may be configured to collect data regarding temperatures of the soil, and the one or more electroconductivity sensors 130 may be configured to collect data regarding electroconductivity levels of the soil.

Figure 4:
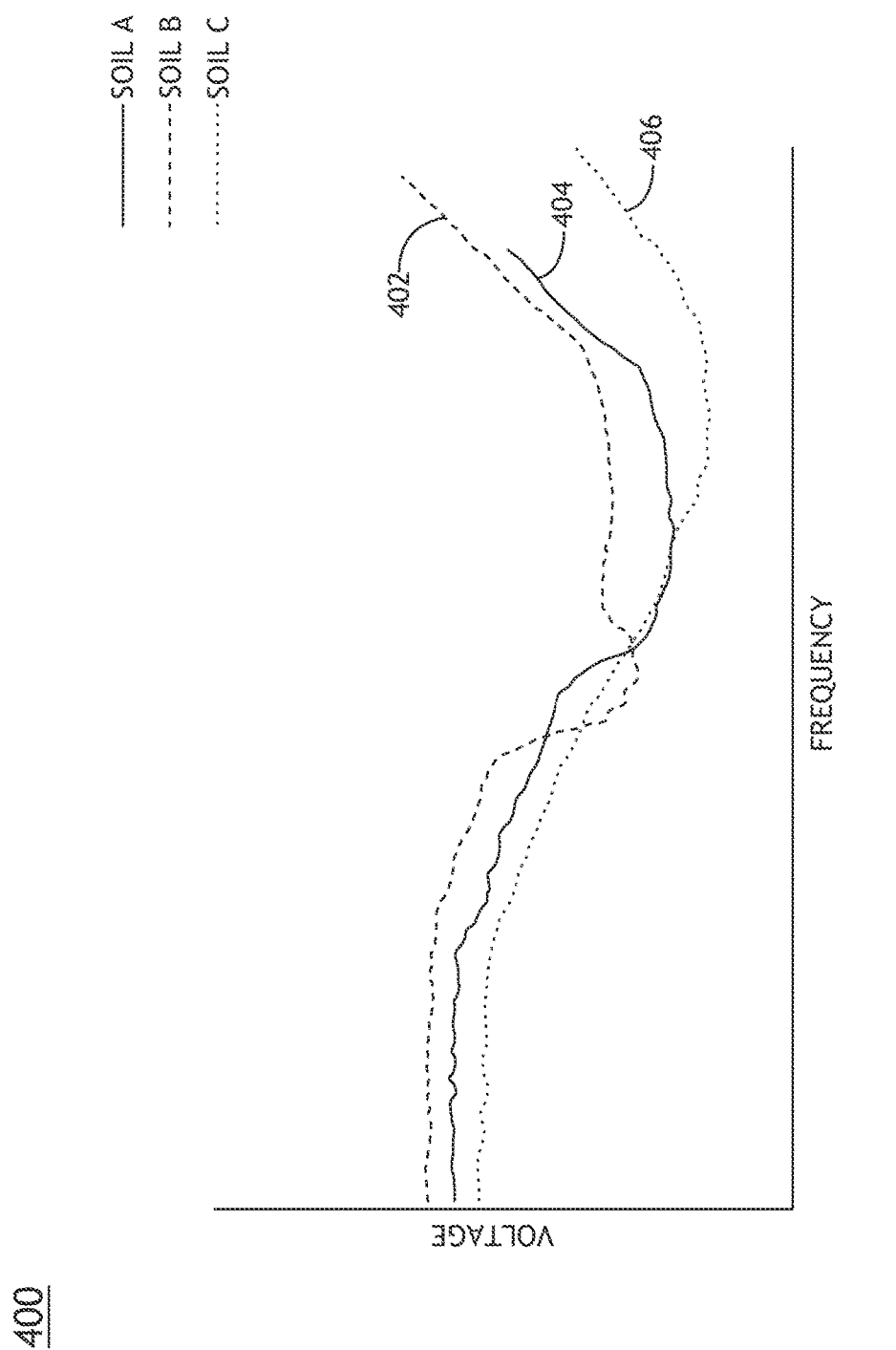
FIG. 4 depicts a graph illustrating multiple soil spectra, in accordance with one or more embodiments of the present disclosure.

In another embodiment, the one or more processors 132 are configured to receive data collected by the one or more sensors 124 and store time-stamped data in memory 134. In another embodiment, the one or more processors 132 may be configured to execute a set of program instructions stored in memory 134, the set of program instructions configured to cause the one or more processors 132 to carry out one or more steps of the present disclosure. For example, as noted previously herein, the one or more moisture sensors 126 may measure soil moisture levels and soil type based on calculated capacitance levels and measured attenuation. In this regard, the one or more processors 132 may be configured to receive voltage level readings from the capacitive soil moisture sensors 126 and generate a graph of frequencies with their corresponding voltages as illustrated in FIG. 4. The one or more processors 132 may then be further configured to compare the generated graph with data stored in memory 134 in order to determine soil type.

In another embodiment, the sensor probe 102 includes a power supply 136. It is noted herein that the power supply 136 may include any power supply known in the art including, but not limited to, one or more batteries, one or more battery packs, one or more energy-storing capacitors, and the like. It is contemplated herein that any power supply which is capable of long-lasting storage capabilities may be used in sensor probe 102, unless noted otherwise herein. In an additional and/or alternative embodiment, it is contemplated herein that sensor probe 102 may be configured to harvest electrical energy from its environment. For example, the power supply 136 may further include an energy harvesting apparatus which is configured to harvest electrical energy from the ground or soil. It is contemplated herein that the power supply 136 may include one or more power supplies which are sized and configured to supply the sensor probe 102 with enough electrical energy to allow the sensor probe 102 to operate sub-surface for several years without requiring recharging, adjusting, or the like.

In another embodiment, the power supply 136 may include a power supply which is configured to enable remote charging capabilities. It is noted herein that a power supply 136 enabled with remote charging capabilities may allow the sensor probe 102 to be charged without having to removed or uncovered from the material. For example, power supply 136 may include a power supply which may be inductively charged by a device above the surface. For instance, an inductive charging device may be placed on the underside of farming equipment (e.g., harvesting equipment, tilling equipment, and the like) such that the inductive charging device may inductively charge the power supply 136 as the farming equipment to which the inductive charging device is attached passes over the sensor probe 102.

It is noted herein that any power and data transmission protocol known in the art may be utilized by sensor probe 102 in order to facilitate power and data transfer among the various components of the sensor probes 102. For example, an SDI-12, RS232, or other protocol may be utilized to facilitate power and data transfer between the one or more sensors 124, the one or more processors 132, memory 134, power supply 136, GPS device 138, and communication device 140.

Figure 3A:
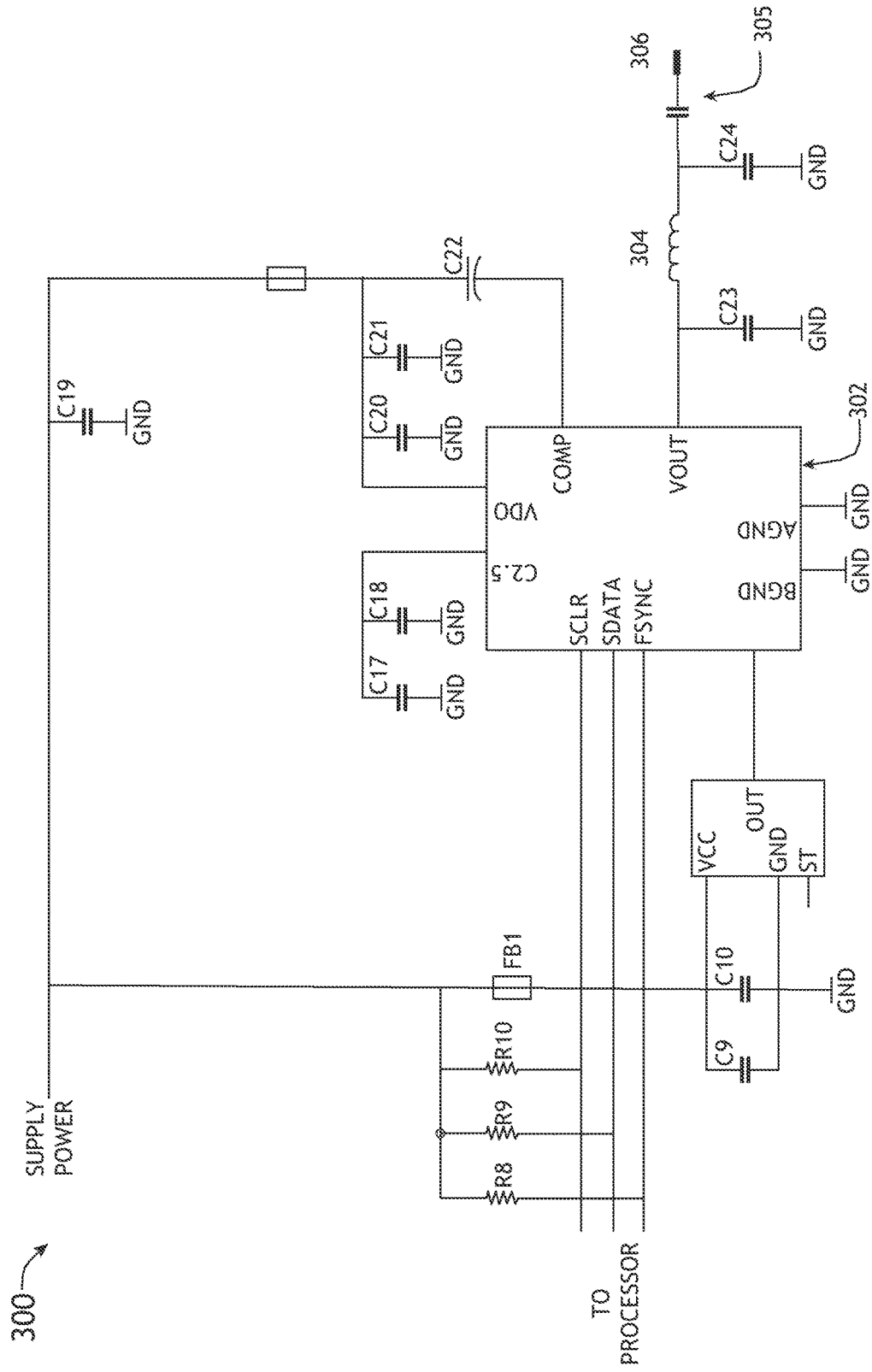
FIG. 3A illustrates a simplified circuit view of a sensor, in accordance with one or more embodiments of the present disclosure.
Figure 3B:
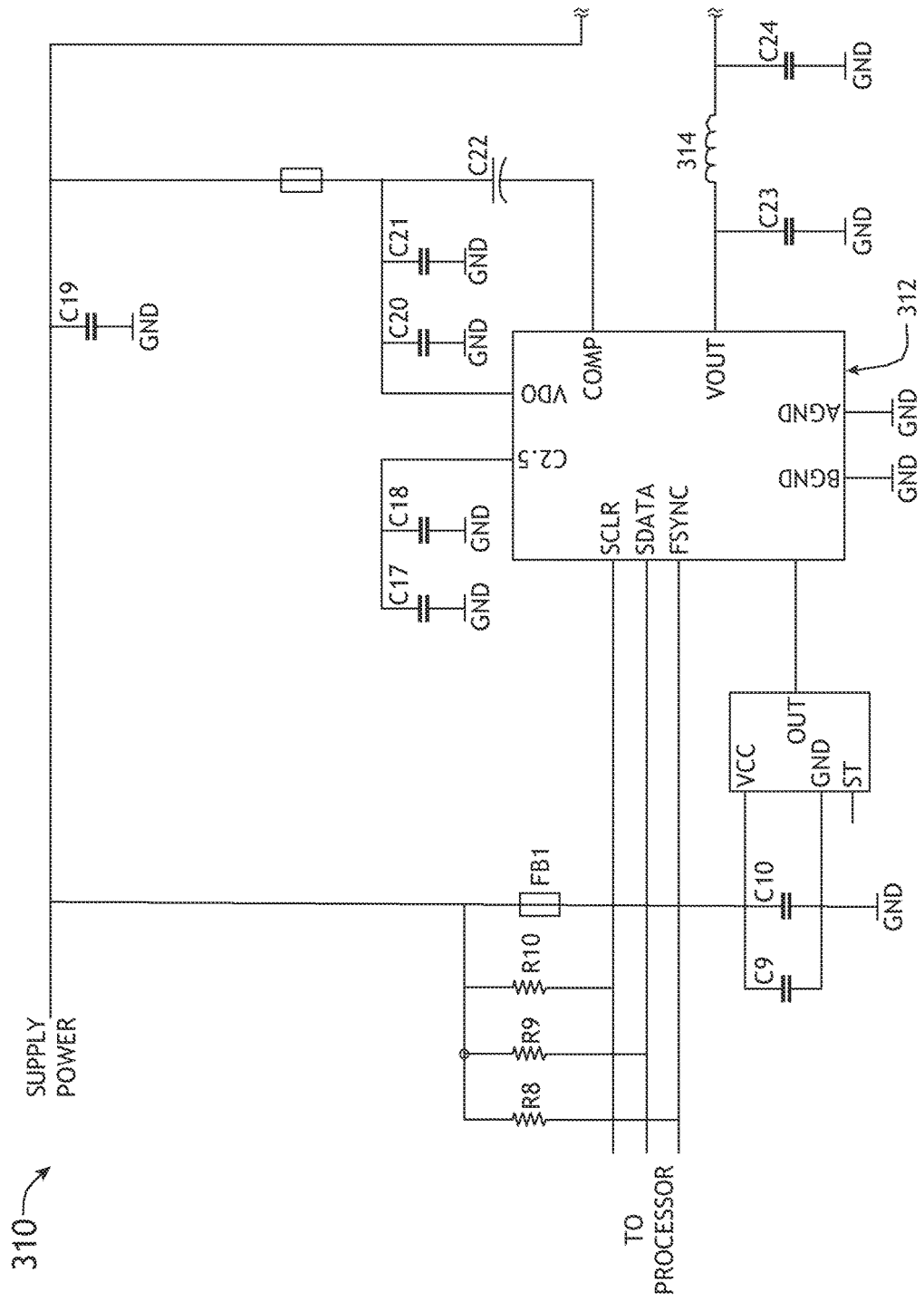
FIG. 3B illustrates a simplified circuit view of a sensor, in accordance with one or more embodiments of the present disclosure.
Figure 3B:
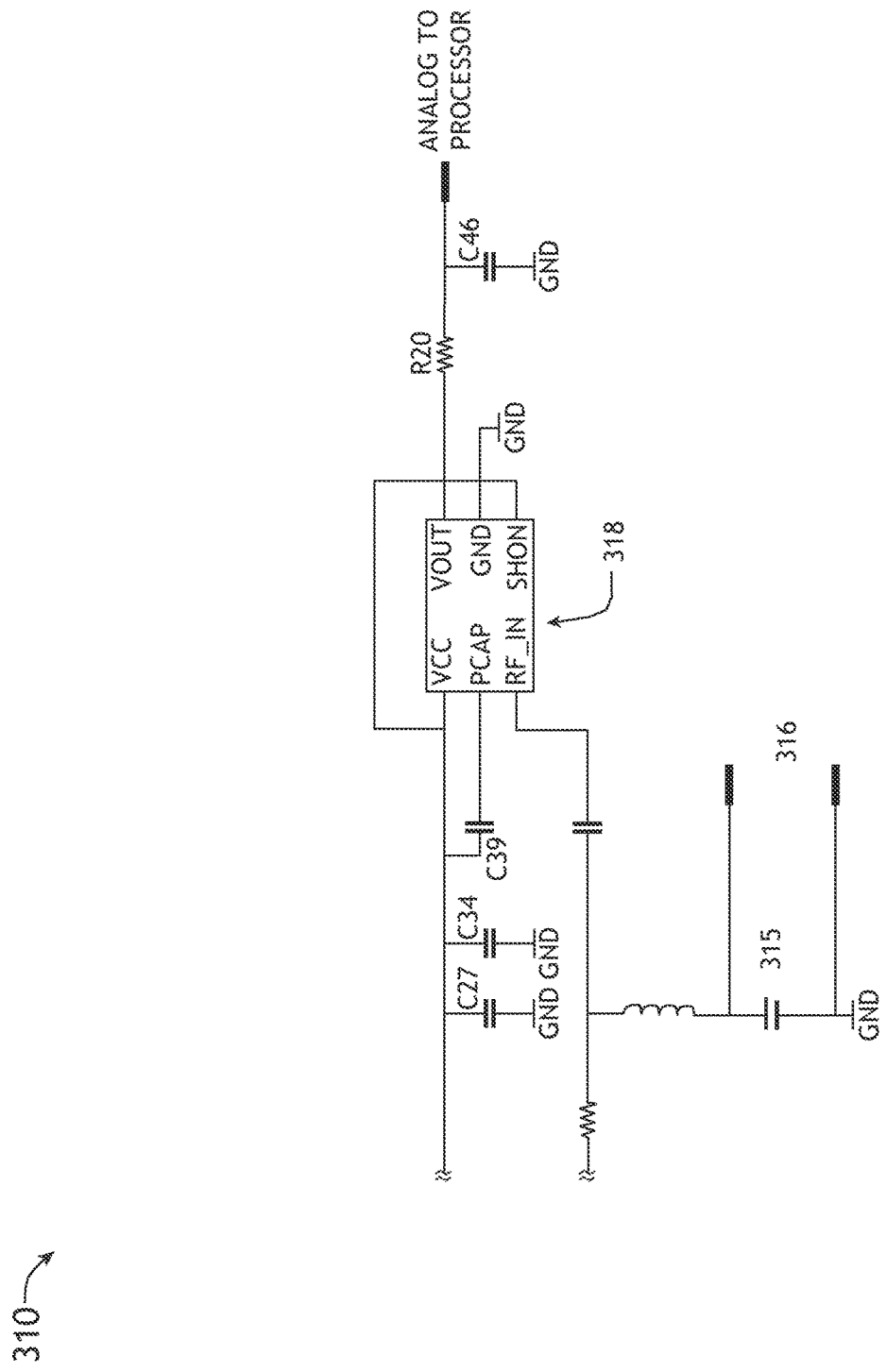

FIGS. 3A and 3B illustrate simplified views of electrical circuits of moisture sensors 300 and 310, respectively. It is noted herein that moisture sensors or probes, including soil moisture probes, may measure frequency and/or attenuation of a radio-frequency signal transmitted through soil in order to measure the level of moisture in the soil.

The moisture sensors 300 and 310 illustrated in FIG. 3A and FIG. 3B, respectively, may resolve many of the shortfalls with the existing variations of moisture sensors. It is further contemplated herein that the moisture sensors 300 and 310 may be used as moisture sensor 126 within one or more sensor probes 102, which may be used within system 100, as illustrated in FIG. 2D. It noted, however, that the sensors 300 and 310 are not limited in operation to probe or system 100 and may be implemented in any number of material sensing contexts.

FIG. 3A illustrates a simplified view of an electrical circuit of a moisture sensor 310 for a moisture sensor 126 of a sensor probe 102, in accordance with one or more embodiments of the present disclosure.

In one embodiment, moisture sensor 300 may include an oscillator 302, a harmonic attenuator 304, one or more resistors, one or more capacitors, and a transmitting antenna 306. Moisture sensor 300 may be powered by power supply 136, as shown in FIG. 2D.

In one embodiment, the oscillator 302 may be used to generate a sweeping range of frequencies. The sweeping range of frequencies may pass through harmonic attenuator 304 and be transmitted using antenna 306. The oscillator 302 may include, but is not limited to, a spectrum-sweep oscillator 302, a direct digital synthesis oscillator 302, and the like. In one embodiment, moisture sensor 300 is configured to measure moisture levels of a material (e.g., soil) and type of material located within an area of interest surrounding the probe capacitor 305. The oscillator 312 may generate a periodic wave (e.g., sinusoidal wave).

In one embodiment, the oscillator 302 is controlled by a processor (e.g., one or more processors 132, or the like) to independently sweep over a determined range of frequencies. As compared to existing variations of moisture sensors, within which the frequency of the oscillator must be fixed in order to yield accurate results, the frequency of the oscillator 302 is controlled by a processor and is able to be generated and swept independently of any characteristics of the circuit.

In one embodiment, the oscillator 302 is configured to sweep across a determined range of frequencies until a resonant frequency of the LC circuit 304, 305 is reached. It is contemplated that the oscillator 302 may be able to sweep across a wide range of frequencies, and may be able to facilitate variable amplitude levels. For example, oscillator 302 may be configured to generate frequencies between 0 MHz and 200 MHz at up to 0.6 V peak to peak amplitude. For instance, oscillator 302 may be configured to generate frequencies between 0 MHz and 12 MHz.

In one embodiment, the output of the oscillator 302 is directed to the LC circuit including the inductor 304 and the probe capacitor 305, which is then directed to transmitting antenna 306. In one embodiment, as the oscillator 302 sweeps across a determined range of frequencies, the oscillator 302 may reach a resonant frequency of the LC circuit made up of inductor 304 and probe capacitor 305. At the resonant frequency, the magnitude of the impedance of the inductor 304 will equal the magnitude of the impedance of the probe capacitor 305. In this regard, as the oscillator 302 approaches the resonant frequency of the LC circuit made up of inductor 304 and probe capacitor 305, the impedance of the LC circuit may approach zero ohms. Accordingly, at the resonant frequency, the inductive reactance and the capacitive reactance cancel one another out, resulting in a zero or near-zero-ohm value.

In one embodiment, the signal generated by the oscillator 302 and passed through the LC circuit comprising inductor 304 and probe capacitor 305 may be transmitted from antenna 306. This signal may then be received by another moisture sensor circuit. For example, as shown in FIG. 3B, when oscillator 312 is turned off, probe element 316 may receive the signal transmitted by antenna 306 in FIG. 3A.

It is noted herein that an inductor (e.g., inductor 304) wired in series with a capacitor (e.g., probe capacitor 305) forms a tank circuit which may be resonant at a particular frequency (e.g., resonant frequency) based upon the inductance of the inductor (e.g., inductor 304) and the capacitance of the capacitor (e.g., probe capacitor 305). In this regard, it is further noted herein that soil moisture levels in the area of interest surrounding the probe capacitor 305 may be determined by analyzing the relationship between the inductor 304 and the probe capacitor 305 at the resonant frequency.

FIG. 3B illustrates a simplified view of an electrical circuit of a moisture sensor 310 for a moisture sensor 126 of a sensor probe 102, in accordance with one or more embodiments of the present disclosure.

In one embodiment moisture sensor 310 may include an oscillator 312, a harmonic attenuator 314, probe elements 316, and an RF detector 318. Moisture sensor 310 may be powered by power supply 136, as shown in FIG. 2D.

The oscillator 312 may be used to generate a sweeping range of frequencies. The amplitude and frequency of oscillator 312 may be controlled by processor(s) 132. The sweeping range of frequencies may pass through harmonic attenuator 312 to reach RF Detector 318. Receiving probe element 316 may receive a frequency signal from moisture sensor 310. An RF detector 318 will then send a voltage reading to processor(s) 132. The oscillator 312 may include, but is not limited to, a spectrum-sweep oscillator 312, a direct digital synthesis oscillator 312, and the like. The oscillator 312 may generate a periodic wave (e.g., sinusoidal wave).

In one embodiment, moisture sensor 310 is configured to measure moisture levels of a material (e.g., soil) located within an area of interest surrounding the probe capacitor 315. Further, moisture sensor 312 is configured to receive a signal from moisture sensor 300 and output a voltage from RF Detector 318 which may be used to generate a graph to determine soil type as shown in FIG. 4. For example, as illustrated by FIGS. 3A and 3B, when oscillator 312 is configured to be off, antenna 306 in moisture sensor 300 may transmit a signal that is to be received by probe element 316 in moisture sensor 310.

In one embodiment, the oscillator 312 is controlled by a processor (e.g., one or more processors 132, or the like) to independently sweep over a determined range of frequencies. As compared to existing variations of moisture sensors, within which the frequency of the oscillator must be fixed in order to yield accurate results, the frequency of the oscillator 312 is controlled by a processor and is able to be generated and swept independently of any characteristics of the circuit.

In one embodiment, the oscillator 312 is configured to sweep across a determined range of frequencies until a resonant frequency of the LC circuit made up of inductor 314 and probe capacitor 315 is reached. It is contemplated that the oscillator 312 may be able to sweep across a wide range of frequencies, and may be able to facilitate variable amplitude levels. For example, oscillator 312 may be configured to generate frequencies between 0 MHz and 200 MHz at up to 0.6 V peak to peak amplitude. For instance, oscillator 312 may be configured to generate frequencies between 0 MHz and 12. MHz.

In one embodiment, the output of the oscillator 312 is directed to the LC circuit including the inductor 314 and the probe capacitor 315. In another embodiment, the LC circuit is electrically coupled to a series resistor. In one embodiment, as the oscillator 312 sweeps across a determined range of frequencies, the oscillator 312 may reach a resonant frequency of the LC circuit. At the resonant frequency, the magnitude of the impedance of the inductor 314 will equal the magnitude of the impedance of the probe capacitor 315. In this regard, as the oscillator 312 approaches the resonant frequency of the LC circuit, the impedance of the LC circuit may approach zero ohms. Accordingly, at the resonant frequency, the inductive reactance and the capacitive reactance cancel one another out, resulting in a zero or near-zero-ohm value.

It is noted herein that an inductor (e.g., inductor 314) wired in series with a capacitor (e.g., probe capacitor 315) forms a tank circuit which may be resonant at a particular frequency (e.g., resonant frequency) based upon the inductance of the inductor (e.g., inductor 314) and the capacitance of the capacitor (e.g., probe capacitor 315). In this regard, it is further noted herein that soil moisture levels in the area of interest surrounding the probe capacitor 315 may be determined by analyzing the relationship between the inductor 314 and the probe capacitor 315 at the resonant frequency.

It is noted herein that the moisture sensors 300 and 310 may provide a number of advantages over existing moisture sensors. For example, the ability to independently control the frequency of the oscillators 302 and 312 may allow the oscillators 302 and 312 to sweep across a wide range of frequencies and identify resonant frequencies for a wide range of soil types, thereby optimizing the performance of the moisture sensors 300 and 310 for a wide variety of soil types. This may be referred to as spectrum analysis.

Furthermore, by independently controlling the frequency of oscillators 302 and 312 to identify resonant frequencies for a wide range of soil types, the moisture sensors 300 and 310 within a sensor probe 102 may be configured to determine soil types at one or more soil depths, based on capacitance readings and oscillator 1102 frequencies, without having to acquire samples and send samples to a lab for analysis. This can be done by transmitting a signal through the soil from moisture sensor 300 to moisture sensor 310. When oscillator 312 is in an off state, moisture sensor 310 behaves as a capacitive moisture sensor. Probe element 316 receives a signal from moisture sensor 300. RF Detector 318 then measures the frequencies over the frequency spectrum and outputs a series of voltages used to create an output graph as shown in FIG. 4.

FIG. 4 depicts a graph 400 illustrating multiple soil spectra in accordance with one or more embodiments of the present disclosure. More particularly, graph 400 illustrates three different data lines 402, 404, and 406 with voltage readings along a frequency spectrum for three different soil types.

The three different data lines 402, 404, and 406 illustrate voltage readings for three different soil types as the oscillator sweeps through a range of frequencies. In one embodiment, the processors 132 illustrated in FIG. 2D may then compare the generated graph with graphical data from known soil types to determine soil type of the measured specimen. In another embodiment, a machine learning classifier may be used by processors 132 to determine soil type. These embodiments are illustrated in FIGS. 500 and 600, respectively.

Figure 5:
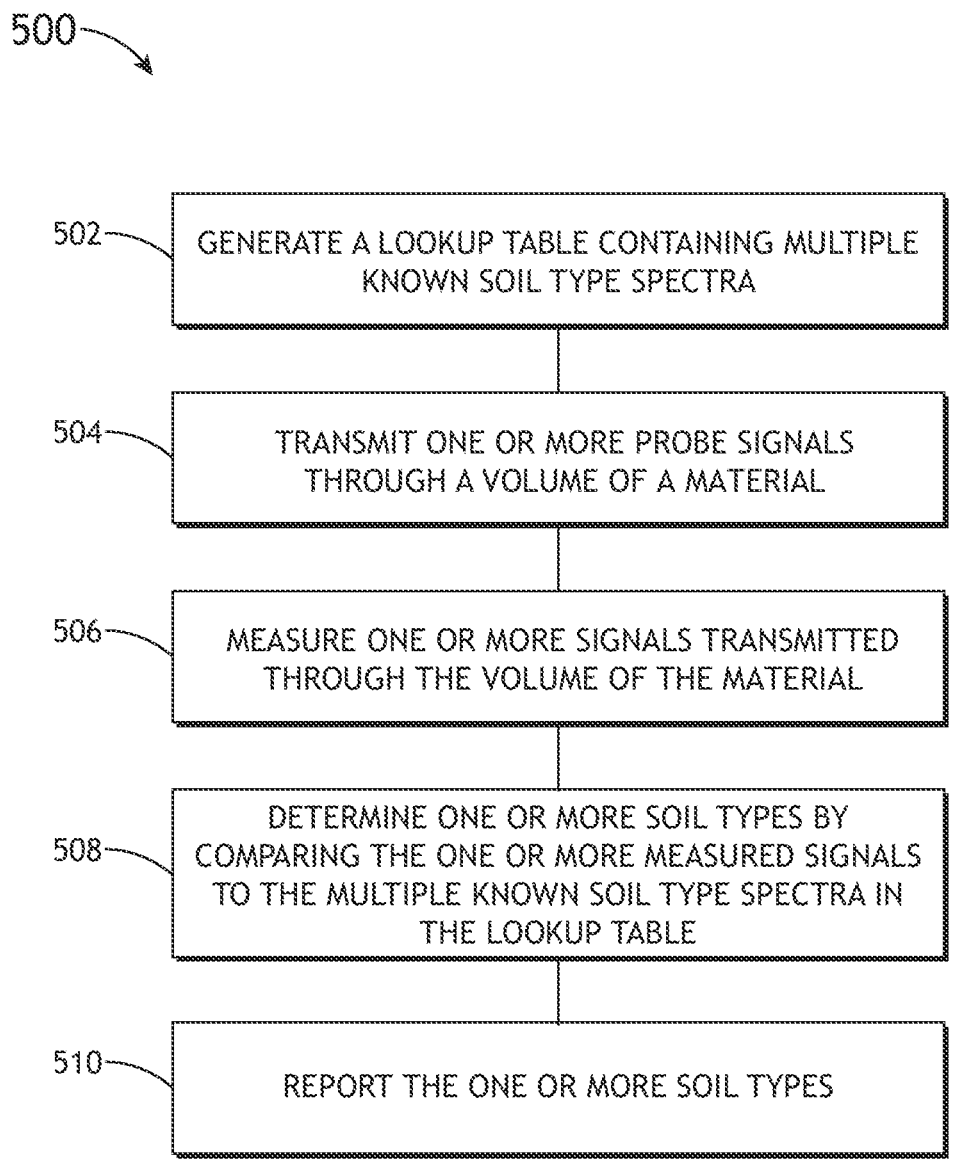
FIG. 5 illustrates a flowchart of a method of determining one or more soil types, in accordance with one or more embodiments of the present disclosure.

FIG. 5 illustrates a flowchart of a method of determining one or more soil types, in accordance with one or more embodiments of the present disclosure. It is noted herein that the steps of method 500 may be implemented all or in part by system 100. It is further recognized, however, that the method 500 is not limited to the system 100 in that additional or alternative system-level embodiments may carry out all or part of the steps of method 500.

In a step 502, a lookup table containing multiple known soil type spectra is generated. For example, as shown in FIG. 2D, a processor 132 in a sensor probe 102 may be configured to generate a lookup table with data for multiple known soil types. This lookup table may then be stored in memory 134 and accessed by processors 132 for determining the soil type of input data from moisture sensors 126.

In a step 504, one or more probe signals are transmitted through a volume of a material. For example, as shown in FIGS. 3A and 3B, a signal from moisture sensor 300 may be transmitted from antenna 306 through a material and received by moisture sensor 310 on probe element 316. As noted previously herein, the material may include, but is not limited to, soil, concrete, compost, sand, volumes of commodities (e.g., grain, rice, wheat, corn, potatoes, sugar beets, DDG, and the like), biomass, landfill material, soil, and the like.

In a step 506, one or more signals transmitted through the volume of a material are measured. For example, as shown in FIG. 3B, the signal received by probe element 316 may be read by RF detector 318. RF detector 318 then may output a voltage (VOUT) that will then be received by one or more processors 132, as illustrated in FIG. 2D.

In a step 508, one or more soil types are determined by comparing the one or more measured signals to the multiple known soil type spectra in the lookup table. For example, as shown in FIG. 2D, memory 134 may be accessed by processors 132. Processors 132 may then compare data from multiple known soil type to the data received by moisture sensors 126 to determine the soil type described by the data received from moisture sensors 126.

In a step 510, the one or more soil types are reported. For example, as illustrated in FIG. 2D and FIG. 1, sensor probe 102 may use communication device 140 to transmit soil type information to a data gateway 104. From there, data gateway 104 may transmit soil type information to a network 106. Network 106 may transmit soil type information to a server 108 and/or a controller 114.

Figure 6:
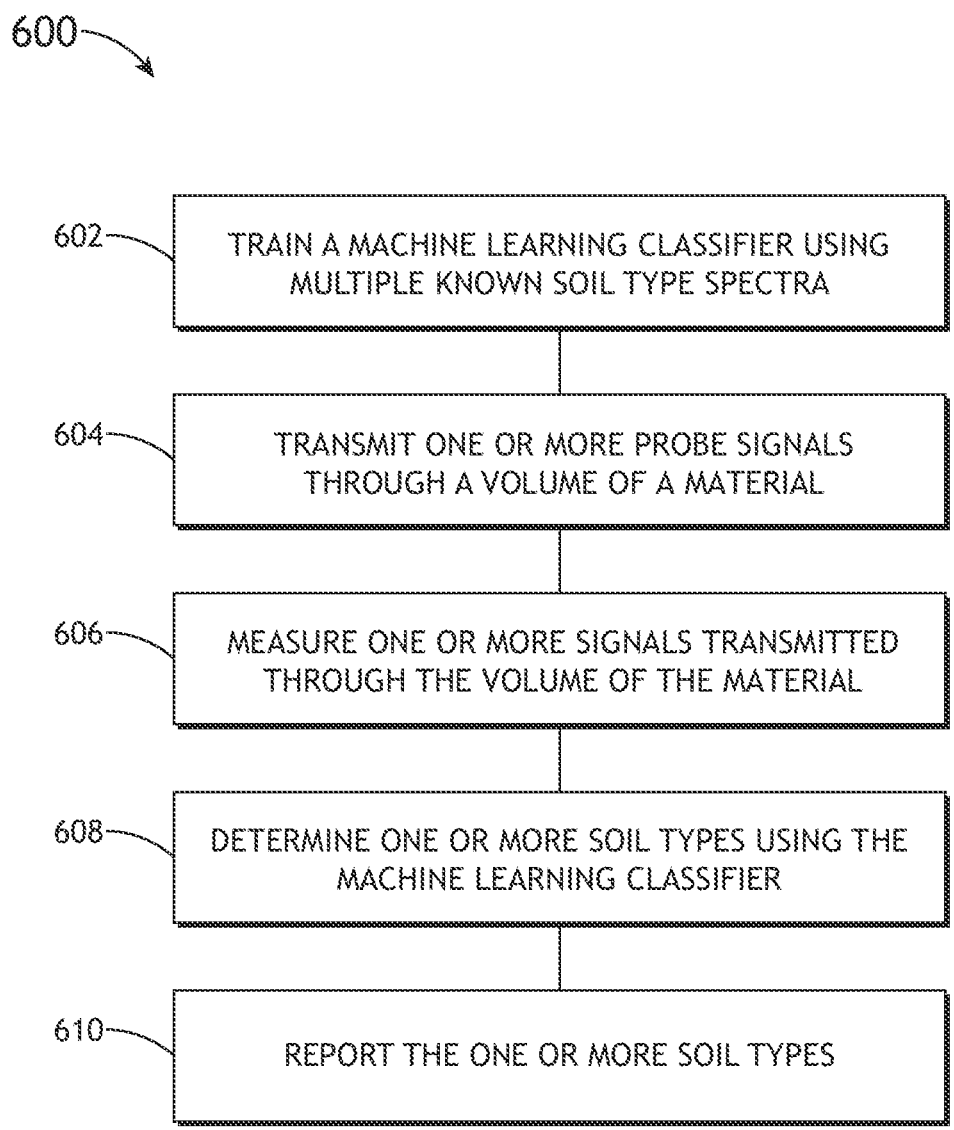
FIG. 6 illustrates a flowchart of a method of determining one or more soil types, in accordance with one or more embodiments of the present disclosure.

FIG. 6 illustrates a flowchart of a method of determining one or more soil types, in accordance with one or more embodiments of the present disclosure. It is noted herein that the steps of method 600 may be implemented all or in part by system 100. It is further recognized, however, that the method 600 is not limited to the system 100 in that additional or alternative system-level embodiments may carry out all or part of the steps of method 600.

In a step 602, a machine learning classifier using multiple known soil type spectra is trained. For example, as shown in FIG. 2D, processors 132 may be used to train a machine learning classifier using multiple known soil type spectra. Processors 132 may then later be used to determine soil type using the machine learning classifier trained by processors 132.

In a step 604, one or more probe signals are transmitted through a volume of a material. For example, as shown in FIGS. 3A and 3B, a signal from moisture sensor 300 may be transmitted from antenna 306 through a material and received by moisture sensor 310 on probe element 316. As noted previously herein, the material may include, but is not limited to, soil, concrete, compost, sand, volumes of commodities (e.g., grain, wheat, corn, potatoes, sugar beets, DDG, and the like), biomass, landfill material, and the like.

In a step 606, one or more signals transmitted through the volume of a material are measured. For example, as shown in FIG. 3B, the signal received by probe element 316 may be read by RF detector 318. RF detector 318 then may output a voltage (VOUT) that will then be received by one or more processors 132, as illustrated in FIG. 2D.

In a step 608, one or more soil types are determined using the machine learning classifier. For example, as shown in FIG. 2D, processors 132 may receive input from moisture sensors 126. The input from moisture sensors 126 may then be used to determine soil type using the machine learning classifier trained by processors 132.

In a step 610, the one or more soil types are reported. For example, as illustrated in FIG. 2D and FIG. 1, sensor probe 102 may use communication device 140 to transmit soil type information to a data gateway 104. From there, data gateway 104 may transmit soil type information to a network 106. Network 106 may transmit soil type information to a server 108 and/or a controller 114.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

All of the methods described herein may include storing results of one or more steps of the method embodiments in memory. The results may include any of the results described herein and may be stored in any manner known in the art. The memory may include any memory described herein or any other suitable storage medium known in the art. After the results have been stored, the results can be accessed in the memory and used by any of the method or system embodiments described herein, formatted for display to a user, used by another software module, method, or system, and the like. Furthermore, the results may be stored "permanently," "semi-permanently," temporarily," or for some period of time. For example, the memory may be random access memory (RAM), and the results may not necessarily persist indefinitely in the memory.

It is further contemplated that each of the embodiments of the method described above may include any other step(s) of any other method(s) described herein. In addition, each of the embodiments of the method described above may be performed by any of the systems described herein.

One skilled in the art will recognize that the herein described components operations, devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

The herein described subject matter sometimes illustrates different components contained within, or connected with, other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected," or "coupled," to each other to achieve the desired functionality, and any two components capable of being so associated can also be viewed as being "couplable," to each other to achieve the desired functionality. Specific examples of couplable include but are not limited to physically mateable and/or physically interacting components and/or wirelessly interactable and/or wirelessly interacting components and/or logically interacting and/or logically interactable components.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," and the like). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, and the like" is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, and the like). In those instances where a convention analogous to "at least one of A, B, or C, and the like" is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, and the like). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes. Furthermore, it is to be understood that the invention is defined by the appended claims.

What is claimed:

1. A sensor probe comprising:
   one or more first sensor circuits;
   one or more second sensor circuits;
   a power supply;

wherein at least one of the first sensor circuits comprises:
one or more oscillators configured to generate a periodic wave; and
a transmitter configured to transmit one or more signals,
wherein at least one of the second sensor circuits comprises:
one or more oscillators configured to generate a periodic wave; and
a probe element configured to receive the one or more signals via at least one of the transmitters of the one or more first sensor circuits or a transmitter of one or more additional first sensor circuits of an additional sensor probe,
a processor communicatively coupled to the one or more first sensor circuits or the one or more second sensor circuits, wherein the processor is configured to:
adjust one or more characteristics of at least one of the one or more first sensor circuits or the one or more second sensor circuits based on data collected by at least one of the one or more first sensor circuits or the one or more second sensor circuits.

2. The sensor probe of claim 1, wherein the processor is configured to control at least one of a frequency, an amplitude, or the power supply to the one or more oscillators.

3. The sensor probe of claim 2, wherein the probe element acts as an antenna to external radio frequency signals when the one or more oscillators are in a powered off mode.

4. The sensor probe of claim 1, wherein the probe element acts as a receiver to the transmitter of the first sensor circuit of at least one of the sensor probe or the additional sensor probe, when the one or more oscillators are in a powered on mode.

5. The sensor probe of claim 4, wherein the transmitter of the one or more first sensor circuits, located on the sensor probe, communicates to the probe element of the one or more second sensor circuits, located on the same sensor probe.

6. The sensor probe of claim 4, wherein the transmitter of the one or more additional first sensor circuits, located on the additional sensor probe, communicates to the probe element of the one or more second sensor circuits, located on the sensor probe.

7. The sensor probe of claim 1, wherein the probe element further comprises: a fringe capacitor configured to change capacitance based on a first moisture level of material located in a first area of interest proximate to the capacitor; and an inductor in series with the capacitor.

8. The sensor probe of claim 7, wherein the oscillator is configured to sweep over a range of frequencies until a resonant frequency of the inductor or the capacitor is reached.

9. The sensor probe of claim 8, wherein a frequency spectrum is derived from a resonant frequency calculated from a completely dry soil condition to the resonant frequency calculated in a completely saturated soil condition.

10. The sensor probe of claim 1, wherein the second circuit comprises a detector device configured to measure a radio frequency strength of the one or more signals, wherein the detector device is configured to determine where a circuit becomes resonant.

11. The sensor probe of claim 1, wherein at least one of the one or more oscillators includes a spectrum-sweep oscillator.

12. The sensor probe of claim 1, wherein the transmitter is configured to transmit frequencies from 10 MHz to 500 MHz.

13. The sensor probe of claim 1, wherein at least one of the one or more first sensor circuits or the one or more second sensor circuits communicate to a plurality of additional sensors, the plurality of additional sensors including at least one of a temperature sensor, an electro-conductivity sensor, a nutrient sensor, an environmental sensor, a soil moisture sensor, or a soil matric potential sensor.

14. The sensor probe of claim 1, wherein the processor is configured to sample a plurality of frequencies between the transmitter and the probe element, wherein the sample of the plurality of frequencies is used by the processor to generate a voltage by frequency graph.

15. The sensor probe of claim 14, wherein at least one of the one or more first sensor circuits or the one or more second sensor circuits are configured to lookup the voltage by frequency graph in at least one of an on board or external table.

16. The sensor probe of claim 14, wherein at least one of the one or more first sensor circuits or the one or more second sensor circuits are configured to lookup the voltage by frequency graph to reference at least one of a soil type, a grain type, stored crop characteristics, feedstuff characteristics, density of construction, or roadway material characteristics.

17. A system, comprising:
a data gateway; and
a plurality of probes communicatively coupled to the data gateway, wherein at least one probe of the plurality of probes comprises:
one or more first sensor circuits;
one or more second sensor circuits;
wherein at least one of the first sensor circuits comprises:
one or more oscillators configured to generate a periodic wave; and
a transmitter configured to transmit one or more signals,
wherein at least one of the second sensor circuits comprises:
one or more oscillators configured to generate a periodic wave; and
a probe element configured to receive the one or more signals via at least one of the transmitter of the one or more first sensor circuits or a transmitter of one or more additional first sensor circuits of an additional sensor probe;
a power supply; and
a processor communicatively coupled to the one or more sensor circuits, wherein the processor is configured to:
receive data collected by at least one of the one or more first sensor circuits or the one or more second sensor circuits;
store data received by at least one of the one or more first sensor circuits or the one or more second sensor circuits; and
generate one or more signals configured to adjust one or more characteristics of at least one of the one or more first sensor circuits or the one or more second sensor circuits based on data collected by at least one of the one or more first sensor circuits or the one or more second sensor circuits.

18. The system of claim 17, wherein the processor is communicatively coupled to the one or more sensor circuits via a network.

19. The system of claim 17, wherein the processor is directly coupled to the one or more sensor circuits via a wired or wireless connection.

20. The system of claim 17, further comprising a user interface, wherein the processor is configured to generate the one or more signals configured to adjust one or more characteristics of at least one probe of the plurality of probes in response to one or more input commands received via the user interface.

21. A method for collecting data associated with one or more sub-surface characteristics of a material comprising:
generating a lookup table based on a plurality of known soil type values;
transmitting one or more signals through a volume of soil with one or more first sensor circuits or one or more second sensor circuits;
measuring the one or more signals through the volume of soil with the one or more first sensor circuits or the one or more second sensor circuits;
adjusting one or more characteristics of at least one of the one or more first sensor circuits or the one or more second sensor circuits based on data collected by at least one of the one or more first sensor circuits or the one or more second sensor circuits; and
determining one or more soil types by comparing the one or more measured signals to the plurality of known soil type values in the lookup table.

\* \* \* \* \*